(12) United States Patent
Thomas et al.

(10) Patent No.: US 10,081,789 B2
(45) Date of Patent: Sep. 25, 2018

(54) FILTRATION OF CELL CULTURE SUPERNATANTS

(71) Applicant: Greenovation Biotech GmbH, Freiburg im Breisgau (DE)

(72) Inventors: Grosse Thomas, Freiburg (DE); Niederkrüger Holger, Freiburg (DE); Schaaf Andreas, Freiburg (DE)

(73) Assignee: GREENOVATION BIOTECH GMBH, Freiburg im Breisgau (DE)

( * ) Notice: Subject to any disclaimer, the term of this patent is extended or adjusted under 35 U.S.C. 154(b) by 0 days.

(21) Appl. No.: 14/414,261

(22) PCT Filed: Jul. 19, 2013

(86) PCT No.: PCT/EP2013/065264
§ 371 (c)(1),
(2) Date: Jan. 12, 2015

(87) PCT Pub. No.: WO2014/013045
PCT Pub. Date: Jan. 23, 2014

(65) Prior Publication Data
US 2015/0147811 A1 May 28, 2015

(30) Foreign Application Priority Data
Jul. 20, 2012 (EP) .................... 12177277

(51) Int. Cl.
| | | |
|---|---|---|
| *C12N 1/02* | (2006.01) | |
| *C07K 1/34* | (2006.01) | |
| *C12M 1/00* | (2006.01) | |
| *C12N 5/04* | (2006.01) | |

(52) U.S. Cl.
CPC ............. *C12N 1/02* (2013.01); *C07K 1/34* (2013.01); *C12M 47/02* (2013.01); *C12M 47/10* (2013.01); *C12N 5/04* (2013.01)

(58) Field of Classification Search
None
See application file for complete search history.

(56) References Cited

U.S. PATENT DOCUMENTS

| | | | | |
|---|---|---|---|---|
| 4,116,831 A * | 9/1978 | Keat | ............ | B01D 29/15 210/771 |
| 5,254,096 A * | 10/1993 | Rondelet | ............ | A61M 5/1456 417/63 |
| 6,692,702 B1 * | 2/2004 | Burshteyn | ............ | B01D 61/147 210/416.1 |
| 6,864,100 B1 * | 3/2005 | Ribbe | ............ | B01D 19/0404 422/503 |
| 2009/0233348 A1 * | 9/2009 | Danner | ............ | C12M 47/06 435/259 |
| 2012/0301907 A1 * | 11/2012 | Sellappan | ............ | G01N 21/76 435/8 |

FOREIGN PATENT DOCUMENTS

| | | |
|---|---|---|
| JP | 2000-279772 A | 3/1999 |
| WO | 2005/108596 | 11/2005 |

OTHER PUBLICATIONS

Buttner-Mainik, Annette et al. Production of biologically active recombinant human factor H in Physcomitrella. Plant Biotechnology Journal (2011) 9, pp. 373-383.*
Buttner-Mainik (Production of biologically active recombinant human factor H in Physcomitrella, 2011).*
Mainik (Production of biologically active recombinant human factor H in Physcomitrella, 2011).*
International Search Report in corresponding International Application PCT/EP2013/065264 dated Sep. 11, 2013.
Written Opinion of the International Searching Authority for corresponding international application PCT/EP2013/065264 dated Jan. 20, 2015.
Lucumi et al., Establishment of long-term perfusion cultures of recombinant moss in a pilot tubular photobioreactor, Process Biochemistry, vol. 41, No. 10, pp. 2180-2187 (Oct. 2006).
Marta Fernandez Nunez, Cytokinin profiling beim Laubmoos Physcomitrella patens (Hedw.) B.S.G.—Einflusse von Cytokinin-Oxidase/Dehydrogenase sowie Adenosin-Kinase, Bibliothekssystem Universitat Hamburg—E-Dissertationen der Universitat Hamberg, pp. FrontPG.-162 (Oct. 2010).
Fischer et al., Affinity-purification of a TMV-specific recombinant full-size antibody from a transgenic tobacco suspension culture, Journal of Immunological Methods, vol. 226, No. 1-2. pp. 1-10 (Jun. 1999).
Kim Sun Tae et al., Secretome analysis of differentially induced proteins in rice suspension-cultured cells triggered by rice blast fungus and elicitor, Proteomics, vol. 9, No. 5, pp. 1302-1313 (Mar. 2009).
Ndimba Bongani et al., Proteomic analysis of changes in the extracellular matrix of *Arabidopsis* cell suspension cultures induced by fungal elicitors, Proteomics, vol. 3, No. 6, pp. 1047-1059 (Jun. 2003).
English Translation of the Written Opinion of the International Searching Authority for corresponding international application PCT/EP2013/065264 dated Jan. 20, 2015.

(Continued)

*Primary Examiner* — Scott Long
*Assistant Examiner* — Nghi V Nguyen
(74) *Attorney, Agent, or Firm* — Nevrivy Patent Law Group P.L.L.C.

(57) ABSTRACT

The invention relates to a method for separating off a liquid supernatant from cells, comprising the steps: providing a mixture of the cells with a liquid, charging a first filter housing with the mixture, wherein in the filter housing a filter having a pore size of between 4 μm and 50 μm is provided on a flat base surface pierced in a sieve manner and the walls of the filter housing are connected so as to seal with the flat base surface that is pierced in a sieve manner, applying a differential pressure of at least 0.5 bar on the mixture, as a result of which the liquid portion of the mixture is forced through the filter and a filter cake containing cells remains in the filter housing, and removal of the filtered liquid.

24 Claims, 3 Drawing Sheets

(56) References Cited

OTHER PUBLICATIONS

Fischer et al., Plant-based production of biopharmaceuticals, Current Opinion in Plant Biology, vol. 7, pp. 1-7 (2004).
Huether et al., Glyco-Engineering of Moss Lacking Plant-Specific Sugar Residues, Plant Biol., vol. 7, pp. 292-299 (2005).
Danquah et al., Dewatering of microalgal culture for biodiesel production: exploring polymer flocculation and tangential flow filtration, J Chem Technol Biotechnol, 84:1078-1083 (2009).
Molina Grima et al., Recovery of microalgal biomass and metabolites: process options and economics, Biotechnology Advances 20:491-515 (2003).
Perlmutter, Barry A., Combination filtration of Pressure, Vacuum and Clarification Technologies for Optimum Process Solutions., BHS Filtration, p. 1-11 (2011).
Japanese Office Action, English Language Translation from Japanese Appl. No. 2015-522110, dated May 23, 2017.
Japanese Office Action from Japanese Appl. No. 2015-522110, dated May 23, 2017.
475855 Miracloth, Overview, Merck Millipore, Retrieved on May 11, 2017, Retrieved from the Internet, URL,<https://www.emdmillipore.com/US/en/product/Miracloth,EMD_BIO-475855?bd=1>.
Fischer F. et al., Affinity-purification of a TMV-specific recombinant full-size antibody from a transgenic tobacco suspension culture, Journal of Immunological Methods, 226:1-10 (1999).
Ueki Atsushi, New Biochemical Experiment Course 17, Microbial Experiment Method, p. 162-164 (1992).
Chemistry in Perspective, Section 3: Organic, Chapter 23: Summary of Some Laboratory Preparations (2012).
Buttner-Mainik A. et al., Production of biologically active recombinant human factor H in Physcomitrella, Plant Biotechnology Journal 9:373-383 (2011).
Office Action from Japanese Appl. No. 2015-522110, dated Feb. 13, 2018.
Translation of Office Action from Japanese Appl. No. 2015-522110, dated Feb. 13, 2018.
Sellstedt, Occurrence and activity of hydrogenase in symbiotic Frankia from field-collected Alnus incana, Physiologia Plantarum 75:304-308 (1989).
Matsushima et al., Pressure Filtration of Culture Broth of Streptomyces, J. Ferment. Technol. 54:42-47 (1976).

* cited by examiner

A:

B:

A:

B:

FILTRATION OF CELL CULTURE SUPERNATANTS

FIELD OF THE INVENTION

The present invention relates to methods for filtration of cell culture supernatants.

BACKGROUND OF THE INVENTION

Using biotechnological methods for production purposes gives rise to a significant opportunity for producing substances which cannot or cannot economically be produced by other means, for example by chemical synthesis, and which are not naturally available in sufficient quantities. The production of plant materials currently focuses on secondary metabolites, wherein the fraction of recombinant expression products is steadily rising. Large-scale production primarily concentrates on plant cell cultures or plants. The possibility for DNA transfer in plants has also meant that quantitative as well as qualitative modifications to plant ingredients are possible. Moreover, plants and plant cell cultures are of interest in the production of heterologous proteins (Fischer et al, Current Opinion in Plant Biology 2004, 7: 1-7).

One strategy involves the production of heterologous proteins in transgenic whole plants. A fundamental disadvantage of using whole plants as described above as an example lies in the need for their time-consuming and cost-intensive cultivation as well as the large areas required for industrial-scale cultivation. Moreover, purification of the desired target substances from whole plants usually involves complex procedural steps, in particular when high demands are placed on the appearance and quality of the products, as is the case with substances used for pharmaceutical or nutritional physiological purposes.

In the second strategy, transgenic plant cell cultures were used for the production of antibodies. A known example is the expression of antibodies or other mammalian proteins (Huether et al, Plant Biol. 2005, 7: 292-299) and their secretion into the medium. Since the purification of heterologous proteins from cells is very costly, the secretion of the target protein into the medium constitutes a significant improvement. Furthermore, safety considerations also favour producing recombinant pharmaceutically relevant proteins in cell cultures, since the transgenic plant cells can be cultured exclusively in bioreactors and do not have to be released. The development of bioreactors for heterotrophic plant cell culture on larger scales has made the required mass cultivation possible.

For further product purification, in a first step, the biomass has to be separated from the supernatant. To this end, various filtration processes are known. In the case of recombinant secreted proteins, the product is present in the culture supernatant. The aim is therefore to retain as little as possible of the residual moisture/supernatant in the separated biomass fraction so as to avoid loss of the product. Various laboratory-scale filtration methods are known. Buettner-Mainik Annette et al, (Plant Biotechnology Journal 9 (3) (2011): 373-383) describe the production of human factor H in *P. patens*. Aqueous cell culture is separated by means of a woven fabric using a suction filter under vacuum. The product obtained was moist and had to be dried. Lucumi et al (Process Biochemistry 41 (10) (2006): 2180-2187) describes a cross-flow filtration during the production of rh VGEF in a *P. patens* bioreactor. Marta Fernandez Nunez (E-dissertation, Hamburg University (2010), p 48, Chapter 2.11.1) describes a vacuum filtration during cytokinin profiling in *P. patens*. Fischer Rainer et al (Journal of Immunological Methods 226 (1-3) (1999): 1-10) concerns a vacuum filtration of tobacco callus cultures which were wet after filtration. WO 2005/108596 AI concerns the in vitro synthesis of cyclic peptides with a cystine knot by expression in plant cells. Cell suspensions were separated with a suction filter under vacuum. Kim Sun Tae et al. (Proteomics 9 (5) (2009): 1302-1313) describes a co-culture of rice cells with the fungus *M. grisea* in suspension. Separation of the secreted proteins was carried out by means of vacuum filtration. Ndimba Bongani K. (Proteomics 3 (6) (2003): 1047-1059) was concerned with an examination of changes in the extra-cellular matrix in *Arabdopsis* in suspension cultures. Vacuum filtration was used to investigate the culture supernatant.

A particular problem lies the fact that in plants and plant cell cultures, in contrast to processes with animal cells and bacteria, the solid residue, e.g. the filter cake in the case of filtration, takes up an immense volume. Thus, large quantities of supernatant are associated with it and retained. One aim of the present invention is thus to improve separation of solid biomass from the culture supernatant.

SUMMARY OF THE INVENTION

The present invention concerns a method for separating a fluid supernatant from cells, comprising the following steps:
a) providing a mixture of the cells with a fluid,
b) charging a filter housing with the mixture, wherein in the filter housing a first filter having a pore size in the range 4 μm to 50 μm is provided on a flat base surface and the walls of the filter housing are connected so as to seal with the flat base surface which is perforated in the manner of a sieve,
c) applying a differential pressure of at least 0.5 bar (500 hPa) to the mixture, as a result of which the fluid portion of the mixture is forced through the filter and a filter cake containing cells remains in the filter housing,
d) removing the filtered fluid.

Filtration with the filter of the invention could also be carried out without the use of a flat base filter (for example with a bag filter) and also without pressure, i.e. filtration purely under gravity. A filtration of this type would, however, suffer from the disadvantage that the residual moisture in the filter cake would be high. As long as the desired purification product is present in the fluid, this means that the loss of product is substantial.

The base surface is preferably perforated in the manner of a sieve. The base surface can constitute a filter in itself, or it can act as a seat and support for a separate filter.

In accordance with the invention, by using the flat filter on a specific base surface in combination with increasing the pressure, the residual moisture retained in the filter cake can surprisingly be reduced to an imperceptible minimum. Extracellular residual moisture contents of 0% (weight %) can be obtained. The intracellular fluid is not counted as residual moisture in this case. In accordance with the invention, the isolation of the residue is improved without intracellular fluid, since the intracellular residual moisture does not constitute a loss of product for selected proteins, and in addition the intracellular cell population could constitute a contaminating mixture.

DETAILED DESCRIPTION OF THE INVENTION

Figure 1:
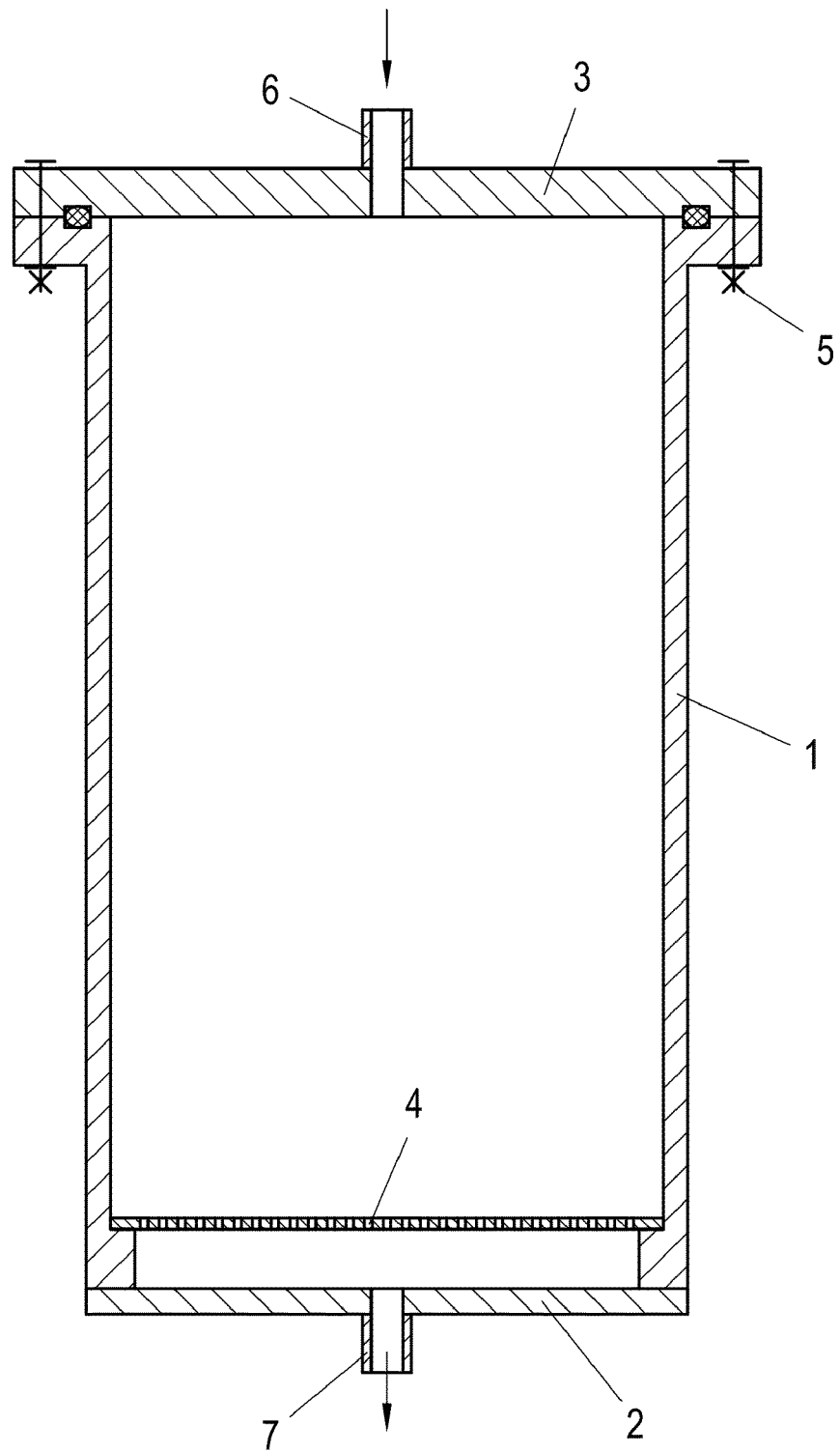
FIG. 1 shows a cross section through a filter housing in accordance with the invention with a base plate (2), a lid (3) and a sieve-like base surface (4) of the charging chamber as a seat for a filter material. The lid is hermetically sealed with the cylindrical housing wall (1) by means of a releasable screw connection (5). The housing also has an inlet (6) and an outlet (7).

In accordance with the invention, in preferred embodiments, the differential pressure is maintained until an extracellular residual moisture of less than 3% (weight %), preferably less than 2%, particularly preferably less than 1% or 0% is obtained in the filter cake. The residual moisture content can be determined as described in Comparative Example 1. In particular, the filter housing of the invention may be used with said filter in order to remove moisture from a filter cake formed by plant cells—in particular down to said residual moisture contents.

In preferred embodiments, the filter is a flat membrane. These are, for example nonwovens, ceramic castings or polymeric membranes which are used in the flat form. They are normally hardly used for large-scale applications. The invention has shown that in plant cell filtration, flat filters can nevertheless be very effectively used, in particular with pressure filtration, and can even produce lower residual moisture contents than, for example, the more usual bag or sack filters.

The filtration system of the invention for the method of the invention was especially developed for large-scale applications. In this manner, in preferred embodiments the dimensions of the filter housing are designed for filtering large volumes of fluid. Particularly preferably, the internal volume of the filter housing is at least 2 L (dm$^3$), especially at least 5 L, at least 8 L, at least 10 L, at least 20 L, at least 30 L, at least 40 L or at least 45 L.

The interior of the housing may be filled continuously or discontinuously with more supernatant for filtration. In preferred embodiments, at least 2 L (dm$^3$) of supernatant is filtered, in special embodiments at least 5 L, at least 8 L, at least 10 L, at least 20 L, at least 40 L, at least 50 L, at least 75 L or at least 100 L is filtered.

Preferably, during the method, the cells are not ruptured. This can be accomplished by handling them gently, at low pressures. Avoiding rupture of the cells is advantageous, because the cell contents do not contaminate the filtration product and further, the cells can be filtered off more efficiently.

Preferably, the absolute pressure at the site for removing the filtered product is at least 0.7 bar (700 hPa). In accordance with the invention, preferably, no vacuum filtration is carried out, but the filtrate remains under high atmospheric pressures of, for example, at least 0.7 bar, at least 0.8 bar, at least 0.9 bar or at least 1 bar. In this manner, evaporation of the fluid (in particular aqueous) filtrate is avoided. This means that the increase in pressure in the filter housing or applied to the mixture in accordance with the invention, in particular at the inlet to the filter housing, results in an absolute positive pressure, i.e. a pressure which is higher than the ambient pressure.

The positive pressure of the invention (differential pressure between the charged supernatant and the filtered fluid) can be produced in different manners. As an example, the pressure may be produced using compressed air (for example fed to the inlet to the filter housing or to a separate air feed opening). In further embodiments, the pressure may be produced by hydraulic pressure, for example as a fluid banking-up pressure or by means of a pump. A further possibility is to increase the pressure by centrifuging. It is also possible to use mechanical pressure, for example using a plunger. Clearly, all these alternatives can also be combined with each other. Preferably, the mixture of cells with the fluid is initially supplied under pressure, and then after introducing the entire mixture to be filtered, more fluid is introduced using compressed air. The compressed air can be applied at the same pressures—identical to or independently of the fluid pressure.

In preferred embodiments, the differential pressure is at least 0.8 bar (800 hPa), preferably at least 1 bar (1000 hPa) or even at least 1.2 bar (1200 hPa). In particular embodiments, the pressure is a maximum of 8 bar, a maximum of 5 bar, a maximum of 3 bar, a maximum of 2 bar or a maximum of 1.5 bar. The pressure difference is essentially determined by the filter used (pore size, dimensions), whereupon a certain counter-pressure arises at a selected positive pressure at the inlet to the filter housing arises. The selected positive pressure can, for example, be measured when the outlet is closed and is preferably an absolute pressure of at least 1.8 bar (1800 hPa), preferably at least 2 bar (2000 hPa), or even at least 3 bar (3000 hPa).

Thus, the filter housing is preferably a pressure vessel, in particular a pressure vessel designed for pressures of at least 2 bar (2000 hPa), particularly preferably at least 5 bar (5000 hPa) or even at least 8 bar (8000 hPa).

The pore size of the first filter is in the range 4 μm to 50 μm. In preferred embodiments, the pore size of the first filter is in the range 6 μm to 40 μm or in the range 8 μm to 30 μm, in particular in the range 9 μm to 250 μm.

In accordance with the invention, the base surface perforated in the manner of a sieve is flat and without any curvature or with hardly any curvature. Preferably, the sieve-like holes are circular in shape. They are preferably at a distance of at least 2 cm from the edge of the base surface which is tightly connected to the wall of the vessel. The sieve-like holes may be 0.001 mm to 5 mm, preferably 0.005 mm to 3 mm or 0.01 mm to 1.5 mm, most preferably 0.03 mm to 0.06 mm in size.

The temperature during the method is preferably in the range 0° C. to 40° C., in particular in the range 10° C. to 30° C., for gentle filtration of the cells.

In accordance with the invention, for the purposes of efficient reduction of the residual moisture content of the filter cake, it is not necessary to wash it any further. Although this step can obviously be carried out, in preferred embodiments the filter cake is not washed with additional fluid. In other embodiments, only small volumes of washing fluid are used, for example a maximum of 1% or a maximum of 0.1% of the volume of the supernatant and/or a maximum of 5% or a maximum of 2% of the volume of the filter cake.

In particularly preferred embodiments, the filtration cited above is followed by a further filtration, in particular intense filtration and/or sterile filtration.

Preferably, the method of the invention comprises the further step of: e1) further filtering of the filtered fluid obtained in step d) with a second filter with a smaller pore size than that of the first filter, wherein the pore size of the second filter is in the range 1 μm to 20 μm. Preferably, the pore size of the second filter is in the range 2 μm to 15 μm, in particular in the range 3 μm to 10 μm, especially in the range 4 μm to 8 μm.

Preferably, the method of the invention comprises the further step of: e2) further filtration of the filtered fluid obtained in step d) or e1) with a third filter with a smaller pore size than that of the second filter, wherein the pore size of the third filter is in the range 0.25 μm to 10 μm. Preferably, the pore size of the third filter is in the range 0.3 μm to 5 μm, in particular in the range 0.35 μm to 2 μm, especially in the range 0.4 μm to 1.5 μm.

Preferably, the method of the invention comprises the further step of: f) further filtration of the filtered fluid obtained in step e1) or e2) with a fourth filter with a smaller pore size than that of the third filter, wherein the pore size of the fourth filter is in the range 0.05 μm to 2 μm. Preferably, the pore size of the fourth filter is in the range 0.08 μm to 1.5 μm, in particular in the range 0.1 μm to 1 μm, especially in the range 0.15 μm to 0.6 μm or to 0.4 μm.

The terms "first", "second", "third" and "fourth" filter do not mean that the method of the invention is limited to this number of filters or that exactly this number of filters are to be used as the filters. It merely serves to differentiate the various filters with the differing pore sizes. Preferably, in the method of the invention, 1, 2, 3, 4 of more filtering steps are undertaken, wherein in preferred embodiments, the filter in a subsequent step has a smaller pore size than that of the filter in the preceding step.

Any filters which are suitable for cell filtration are suitable filter materials for the first, second, third and/or fourth filters. Examples of materials are those formed from cellulosic or polymeric membranes. Examples are polyethersulphone membranes (such as Sartopore filters, for example) or cellulose/diatomaceous earth/pearlite filters (such as Seitz K series filters, for example).

The cell to be employed in the method of the invention is preferably a plant cell, preferably a moss, in particular selected from the group consisting of earth mosses and liverworts, wherein species of the genuses *Physcomitrella, Funaria, Sphagnum* and *Ceratodon*, or *Marchantia* and *Sphaerocarpos* are particularly preferred. *Physcomitrella patens* is particularly preferred. Most particularly preferably, the method of the invention is carried out using cells, plants or plant tissues such as protonema from the earth moss *Physcomitrella patens*. Further preferred plants are tobacco, beans or lentils. Preferably, the plant is an aquatic plant, for example from the genuses *Lemna, Spirodela, Landoltia, Wolffia* or *Wolffiella*.

The method of the invention is particularly suitable for filtering cells having a cell wall. In addition to genuine plant cells, the cells may also be selected from a fungal cell or an algal cell which can be seen as equivalent embodiments. As used herein, "cells" can mean isolated cells, agglomerated cells or one cell in a multi-cellular organism. A "plant cell" may be an individual plant cell or a cell in a plant or in a plant tissue. In analogous manner, a "fungal cell" may be an individual cell in a fungus or a cell in a fungal tissue. The "algal cell" is preferably a green algal cell. The tissues may, for example, be selected from phloem, xylem, mesophyll, phylum, leaves, thallus, protonema, chloronema, caulonema, rhizoid or gametophore tissues. The cells may comprise or consist of protoplasts or parenchymal cells, in particular callus cells.

Further suitable cells are bacterial cells. Although the invention is first and foremost optimized for plant cells, the same advantages, such as gentle treatment of the cells at a high fluid separation ratio, can also be observed in bacterial cells.

Preferably, a recombinant protein produced by the plant cells is present in the fluid supernatant. In this regard, equally or in combination, it is also possible to purify a recombinant protein in the supernatant by filtration of the fluid. The recombinant production of proteins in plants is well known, as discussed above in the introduction, and the usual methods for transformation and expression in plants can be applied.

The present invention further concerns a kit or a system with a filter housing as described hereinabove and a first filter as described hereinabove, for example with a pore size in the range 4 μm to 50 μm. The kit or the system may advantageously also be provided with a second, third and/or fourth filter as described herein. This kit or the system is suitable for carrying out the method of the invention or is used for this purpose.

The invention also concerns the use of the kit of the invention or its components in order to remove moisture from a filter cake formed from (plant) cells.

The present invention will now be illustrated by means of the following figures and examples; these special embodiments of the invention are not limiting in any way.

EXAMPLES

Comparative Example 1

On a small scale, a supernatant with recombinantly produced antibodies (carcinoembryonic antigen (CEA) specific IgG1 H10) was separated from the protonema moss tissue produced with a cell density of up to 7 g/L. A sieve with a pore size of 100 μm was used for this purpose; the remaining residual moisture content was approximately 50%.

When scaling up the production, suitable filter methods were investigated. In this regard, the first filtration step was to be carried out over a relatively coarse filter. This prevented the filter from blocking up and was primarily intended for the separation of moss and supernatant. Intense filtration effects during clarifying filtration were not very significant.

In a first filtration step, a bag filter was used (Eaton; housing type: TBF-0101-AD10-050D, bag filter article no: F5869549; volume 13 L). The filter was located in a housing insert with a curved base surface, wherein the insert was perforated in the manner of a sieve at the base surface and at the insert wall. Filtration was successful, however the residual moisture content in the separated moss was very high and could not be forced out of the moss using compressed air (1-3 bar).

The extracellular residual moisture content was determined after filtration was complete by removing the filter cake and manually forcing it out. A volumetric comparison of the fluid forced out and the retained moss material produced a ratio of approximately 50%. This was associated with high product losses which were not measured separately.

Comparative Example 2

In an analogous manner to Comparative Example 1 in a scaling-up experiment, supernatant with recombinantly produced antibodies was separated from the moss tissue producing it by filtration. An alternative housing insert with a curved base surface was used; this time it was only perforated in the manner of a sieve at the base surface of the insert. This was meant to ensure that the compressed air would escape homogeneously over the filter cake and that the residual moisture was removed from the moss residue. However, this was not in fact the case. The residual moisture content was determined as described in Comparative Example 1 and was also approximately 50% (weight %).

Example 1: Large Volume Filtration

A novel filter housing was developed which was intended to produce a lower residual moisture content in the separated plant cells. The novel housing is shown in FIG. 1. The filter housing is characterized by a sieve-like insert (4) which acts as a flat seat for a filter material. The housing wall does not act as a filtering surface. All of the filtered fluid must pass through the flat base plate on the way to the outlet. In the case of animal cells, this filter would very quickly tend to clog due to the small filtering surface. In the case of plant cells, however, it has been observed that not only is filtration possible with a high volume (>5 L) but, surprisingly, it has the advantage of producing a low residual moisture content.

The housing is equipped with a Seitz K900 filter disc (pore size 8-20 μm; Pall). The housing is designed for a scale of up to 500 L and can be scaled up to any volume of culture supernatant. The tests with this filter housing provided good data. A test run with 500 L of culture liquor and a low biomass (0.5 g/L) as well as several tests with 100 L of culture liquor with high biomasses (4 to 7 g/L) were able to obtain an extracellular residual moisture content of 0% in the filter cake (determined as in Comparative Example 1). This means that the supernatant of the culture liquor in this module was forced in succession through the complete filter cake, then the filter and out of the filter housing. The product losses for an antibody, in mg/L, also turned out to be very low (4% to 13%—step 1 in Table 1). The losses here were solely due to non-specific retention of product in the moss cake or filter, but not due to the culture supernatant being retained in the filter cake.

Example 2: Intense and Sterile Filtration

The filtrate of Example 1 was filtered further in order to carry out intense and sterile filtration: for the intense filtration, filtration was carried out with a Seitz K700 filter disc (pore size 6-12 μm; Pall) and a Seitz KS50 filter disc (pore size 0.4-1 μm; Pall). These filtrations can be carried out sequentially in one housing and in one pass, or separately in separate housings. The gap between the filters was selected so that sufficient space was available for moss cells or cell fragments. The filters were mounted in two parallel runners in accordance with the SUPRAdisc™ (Pall) and the Supracap™ 100 (Pall) systems (Supradisc filter: 300P700S205SP and 200P050S205SP; Supracap filter: NP6P7001 and NP6P0501).

For sterile filtration, the filtrate was further filtered with a Sartopore 2 filter disc (pore size 0.2 μm; Sartorius).

Example 3: Results

The filter housing which has been developed guarantees optimized solid-fluid separation. A solid filter cake is formed which is largely free from residual moisture, and thus the product losses are kept low. The entire process ensures that the further purification steps can be carried out rapidly without clogging the filter.

Figure 2:
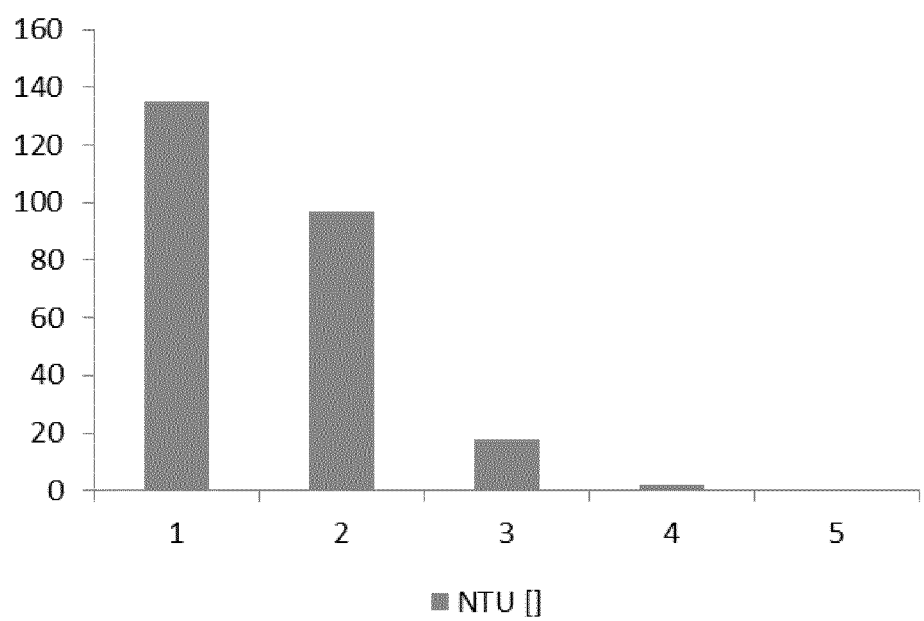
FIG. 2 shows the results of analysis after purification of the suspended material by means of turbidity measurements (NTU [-]; A) as well as the product losses (titre [mg/L]; B) with the Supradisc system during intense filtration. (1=culture supernatant, 2=moss-free K900 filtrate, 3=K700 filtrate, 4=KS50 filtrate, 5=sterile filtrate).
Figure 2:
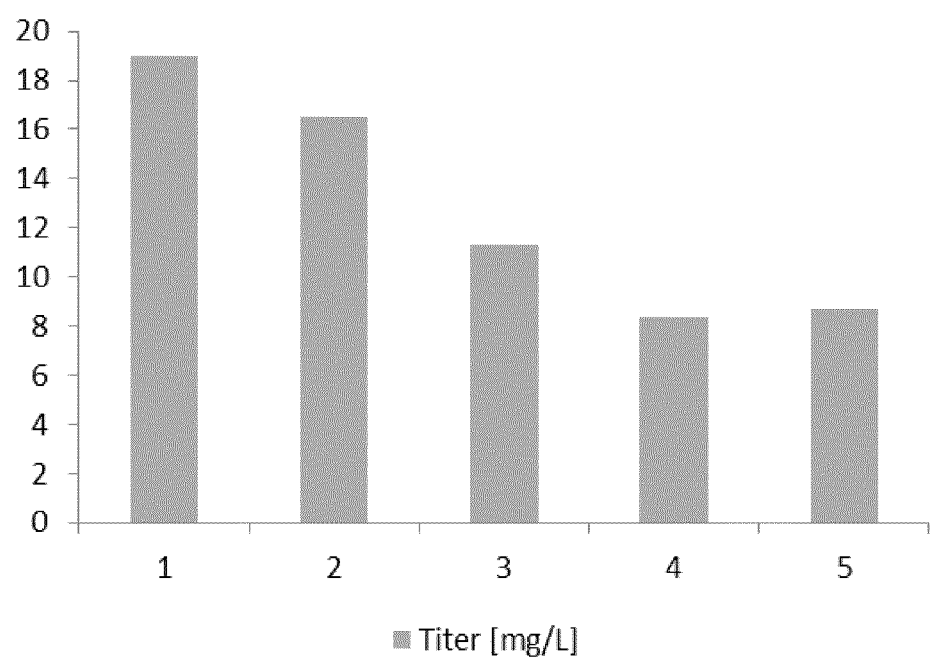
Figure 3:
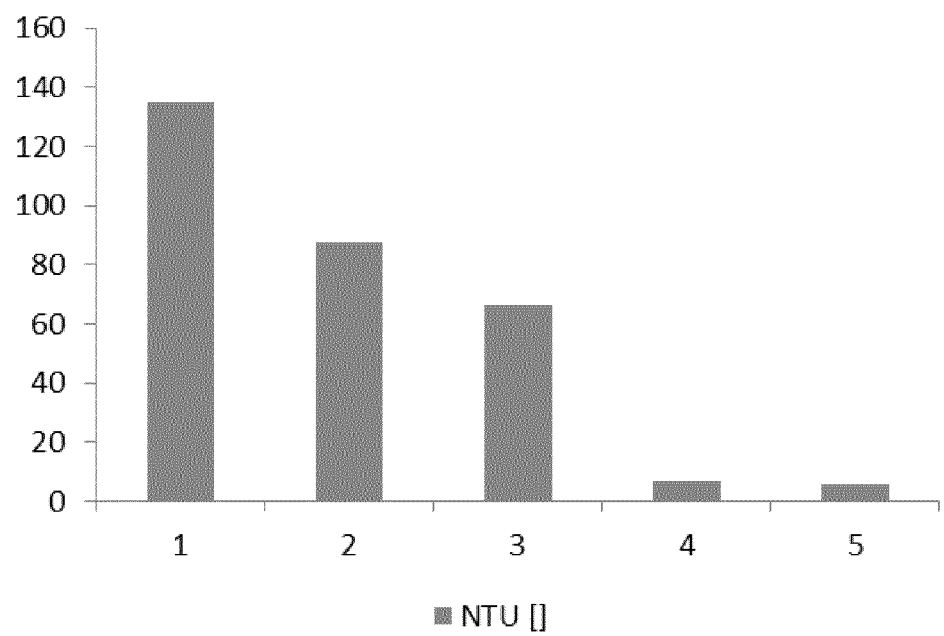
FIG. 3 shows the results of analysis after purification of the suspended material by means of turbidity measurements (NTU [-]; A) as well as the product losses (titre [mg/L]; B) with the Supracap system during intense filtration. (1=culture supernatant, 2=moss-free K900 filtrate, 3=K700 filtrate, 4=KS50 filtrate, 5=sterile filtrate).
Figure 3:
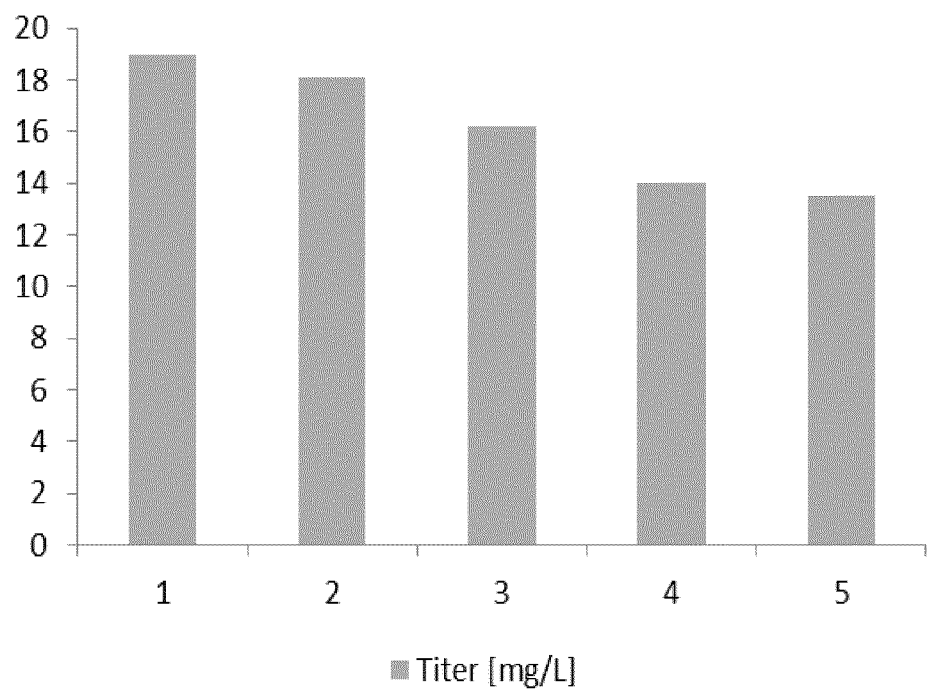

FIGS. 2 and 3 show the results. They show the analysis of the purification of suspended material by filtration by means of turbidity measurements (NTU) and the development of antibody losses by the filtration, each time for purification using the Supradisc system (FIG. 2) and purification using the Supracap system (FIG. 3) during intensive filtration. Table 1 summarizes the product losses.

TABLE 1

Product losses during purification using the Supradisc and Supracap systems

| Filtration step | Supradisc yield [%] | Loss [%] | Supracap yield [%] | Loss [%] |
|---|---|---|---|---|
| 1: K900 | 86.84 | −13.15 | 95.26 | −4.73 |
| 2: K700 | 68.48 | −31.51 | 89.50 | −10.49 |
| 3: KS50 | 74.33 | −25.66 | 86.41 | −13.58 |
| 4: sterile filt'n | 103.57 | 3.57 | 96.42 | −3.57 |
| Total | 45.78 | −54.21 | 71.05 | −28.94 |

The invention claimed is:

1. A method for separating a fluid supernatant from cells, comprising the following steps:
   a) providing a mixture of the cells with a fluid,
   b) loading a filter housing with the mixture, wherein in the filter housing a first filter having a pore size in the range 4 μm to 50 μm is provided on a flat base surface and the walls of the filter housing are connected so as to seal with the flat base surface which is perforated in the manner of a sieve,
   c) applying a differential pressure of at least 0.5 bar to the mixture by compressed air, as a result of which the fluid portion of the mixture is forced through the filter and a filter cake containing cells remains in the filter housing, wherein the absolute pressure at the withdrawal point is at least 0.7 bar, and
   d) removal of the filtered fluid,
until an extracellular residual moisture of less than 3% (weight %) is obtained in the filter cake.

2. The method of claim 1, characterized in that the internal volume of the filter housing is at least 2 L.

3. The method of claim 1, characterized in that at least 10 L of supernatant is filtered.

4. The method of claim 1, characterized in that the cells are not ruptured during the method.

5. The method of claim 1, characterized in that the absolute pressure at the withdrawal point is at least 0.8 bar.

6. The method of claim 1, characterized in that the differential pressure is at least 0.8 bar.

7. The method of claim 1, characterized in that the filter housing is a pressure vessel.

8. The method of claim 1, characterized in that the temperature during the method is in the range 0° C. to 40° C.

9. The method of claim 1, characterized in that the filter cake is not washed by additional fluid and/or wherein fluid is discharged from the filter cake using compressed air.

10. The method of claim 1, further comprising the step of:
   e1) further filtering of the filtered fluid obtained in step d) with a second filter with a smaller pore size than that of the first filter, wherein the pore size of the second filter is in the range 1 μm to 20 μm.

11. The method of claim 10, further comprising the step of: e2) further filtration of the filtered fluid obtained in step d) or e1) with a third filter with a smaller pore size than that of the second filter, wherein the pore size of the third filter is in the range 0.3 μm to 10 μm.

12. The method of claim 10, further comprising the step of: f) further filtration of the filtered fluid obtained in step e1) with a fourth filter with a smaller pore size than that of the third filter, wherein the pore size of the fourth filter is in the range 0.05 μm to 2 μm.

13. The method of claim 1, characterized in that the cells are cells having a cell wall.

14. The method of claim 1, characterized in that a recombinant protein produced by the cells is present in the fluid supernatant and/or in that a recombinant protein is purified out of the supernatant by means of the filtration.

15. The method of claim 1, wherein the filter housing comprises an inlet for the compressed air.

16. A kit comprising filter housing as defined in claim 1 and having an internal volume of greater than 5 L and comprising walls with larger height than the diameter of the flat base surface, and a first filter with a pore size in the range 4 μm to 50 μm, optionally further comprising:
   i) a second filter wherein the pore size of the second filter is in the range 1 μm to 20 μm,
   ii) a third filter wherein the pore size of the third filter is in the range 0.3 μm to 10 μm, and/or
   iii) a fourth filter wherein the pore size of the fourth filter is in the range 0.05 μm to 2 μm, in order to remove moisture from a filter cake formed by cells.

17. The method of claim 11, further comprising the step of: f) further filtration of the filtered fluid obtained in step e1) or e2) with a fourth filter with a smaller pore size than that of the third filter, wherein the pore size of the fourth filter is in the range 0.05 μm to 2 μm.

18. The method of claim 1, characterized in that the differential pressure is at least 1 bar.

19. The method of claim 1, characterized in that the filter housing is a pressure vessel designed for pressures of at least 2 bar.

20. The method of claim 1, characterized in that the filter housing is a pressure vessel designed for pressures of at least 5 bar.

21. The method of claim 13, wherein the cells are selected from the group consisting of plant cells, moss cells, earth moss cells, and *Physcomitrella patens* cells.

22. The method of claim 1, further comprising a step of applying pressure of at least 0.5 bar to the mixture by hydraulic pressure, fluid banking-up pressure or by a pump.

23. The method of claim 1, wherein the filter housing comprises an internal volume of at least 2 L and comprises walls with larger height than the diameter of the flat base surface.

24. The kit of claim 16, wherein the filter housing comprises an inlet for compressed air.

\* \* \* \* \*